United States Patent
Ruiz Bravo

(10) Patent No.: US 11,318,261 B2
(45) Date of Patent: May 3, 2022

(54) SAFETY PEN NEEDLES

(71) Applicant: Pikdare-Società per Azioni, Casnate con Bernate (IT)

(72) Inventor: Alejandro José Ruiz Bravo, Como (IT)

(73) Assignee: PIKDARE-SOCIETÀ PER AZIONI, Casnate con Bernate (IT)

( * ) Notice: Subject to any disclaimer, the term of this patent is extended or adjusted under 35 U.S.C. 154(b) by 85 days.

(21) Appl. No.: 16/782,751

(22) Filed: Feb. 5, 2020

(65) Prior Publication Data
US 2020/0246554 A1 Aug. 6, 2020

(30) Foreign Application Priority Data
Feb. 6, 2019 (IT) .................. 102019000001703

(51) Int. Cl.
*A61M 5/32* (2006.01)
*A61M 5/24* (2006.01)

(52) U.S. Cl.
CPC ............ *A61M 5/3245* (2013.01); *A61M 5/24* (2013.01); *A61M 5/3257* (2013.01); *A61M 2005/3247* (2013.01); *A61M 2005/3254* (2013.01)

(58) Field of Classification Search
CPC .............. A61M 5/3245; A61M 5/3257; A61M 2005/3254; A61M 5/321; A61M 2005/3247; A61M 5/24; A61M 2005/3267; A61M 2205/583; A61M 5/326
See application file for complete search history.

(56) References Cited

U.S. PATENT DOCUMENTS

2008/0249477 A1* 10/2008 Paproski ............... A61M 5/326
604/198
2017/0203054 A1 7/2017 Newman et al.

FOREIGN PATENT DOCUMENTS

DE 102006041810 A1 3/2008
DE 10066400 B4 1/2012

OTHER PUBLICATIONS

Italian Search Report and Written Opinion dated Oct. 25, 2019, in corresponding IT Application No. 102019000001703, 10 pages.

* cited by examiner

*Primary Examiner* — Brandy S Lee
(74) *Attorney, Agent, or Firm* — MH2 Technology Law Group LLP

(57) ABSTRACT

A safety pen needle includes: a main body, a cannula fixed to the main body and at least partially projecting out of the main body, a lock element placed inside the main body, a thrust element placed inside the main body, and a shield movable relative to the main body while remaining at least partially inserted within the main body. The pen needle is configured to move from a first configuration, in which the shield entirely covers an upper end of the cannula, to a second configuration, in which the upper end of the cannula is exposed, due to the action of external thrust. The pen needle is configured to move from the second configuration to an irreversible third configuration, in which the shield entirely covers the upper end of the cannula, due to the action of thrust exerted by the thrust element.

13 Claims, 6 Drawing Sheets

SAFETY PEN NEEDLES

CROSS-REFERENCE TO RELATED APPLICATION(S)

This application claims priority under 35 U.S.C. § 119 from Italian Patent Application No. 102019000001703, filed on Feb. 6, 2019, in the Italian Patent and Trademark Office ("IPTO"), the entire contents of which are incorporated herein by reference.

TECHNICAL FIELD

This invention relates to a safety pen needle mainly usable to inject medication with an injection pen to be used, for example, by diabetic patients to make regular insulin injections.

STATE OF THE ART

In the state of the art, the use of a pen needle mounted on a vial containing a liquid to be injected is known. The injection is made with an injection pen which is coupled to the medication vial to exert on the liquid the necessary pressure in order to subcutaneously inoculate the liquid. The creation of an injection kit is also known. Said kit comprises a pen needle and a vial containing a medication to be injected.

The pen needle comprises a main body, a cannula and a shield. The main body extends in a longitudinal direction between a bottom and an opposite top and comprises a cavity which extends from the bottom to an opening placed at the top.

The cannula is placed inside the cavity and extends between a lower end, fixed to the bottom of the main body, and an opposite top end, projecting out of the cavity through the opening. The shield is configured to be reversibly coupled to the main body and to fully cover the top end of the cannula.

When in use, namely in case of injection, the vial is adapted to the bottom of the container to thereby allow the cannula to withdraw the liquid to be injected. An injection pen is coupled to the free end of the vial to compress the fluid contained inside the vial allowing the fluid to come out through the pen needle cannula. Once the shield has been removed from the main body of the pen needle, it is possible to proceed with the injection.

Problem of the Prior Art

After using a known pen needle, it is necessary to manually reposition the shield on the main body in order to protect the top end of the cannula. In addition, both before and after use, the pen needle is in the same configuration, namely with the shield covering the top end of the cannula. In detail, before use, the top end of the cannula is accessible by removing the shield from the main body. After use, there is a high risk of infection related to accidental punctures that could take place, for example right before disposal. In addition, once the shield has been removed, it is not possible to distinguish between an unused pen needle and one that has been already used so there is a risk of reusing the same pen needle more than once. Reusing the same pen needle involves the use of a cannula that is not sterile. This causes an increased risk of infection following an injection made with a contaminated cannula.

SUMMARY OF THE INVENTION

In this context, the technical task which forms the basis of this invention is to provide a safety pen needle which overcomes the drawbacks of the known art mentioned above.

In particular, the purpose of this invention is to provide a safety pen needle which prevents accidental punctures after the use of the pen needle.

In addition, the purpose of this invention is to provide a safety pen needle that allows to irreversibly cover the cannula of the pen needle after its use.

The purpose of this invention is also to provide a safety pen needle which allows to distinguish between an unused pen needle and one that has been already used.

Advantages of the Invention

Thanks to an embodiment of this invention, it is possible to irreversibly cover the cannula after using the pen needle, removing the risk of accidental punctures and preventing the reuse of the device. This prevents the risk of accidental punctures or contamination caused using the cannula of the non-sterile pen needle Thanks to an additional embodiment of this invention, it's possible to distinguish between the configuration of the pen needle adopted before use from the configuration it adopts after the activation of the safety mechanism, in order to make the activation caused by the snap of the mechanism evident and to prevent further use.

BRIEF DESCRIPTION OF THE DRAWINGS

Further characteristics and advantages of this invention will be evident from the indicative, therefore not restrictive, description, of a preferred, but not exclusive, embodiment of a safety pen needle, as illustrated in the annexed drawings in which.

DETAILED DESCRIPTION

Figure 1:
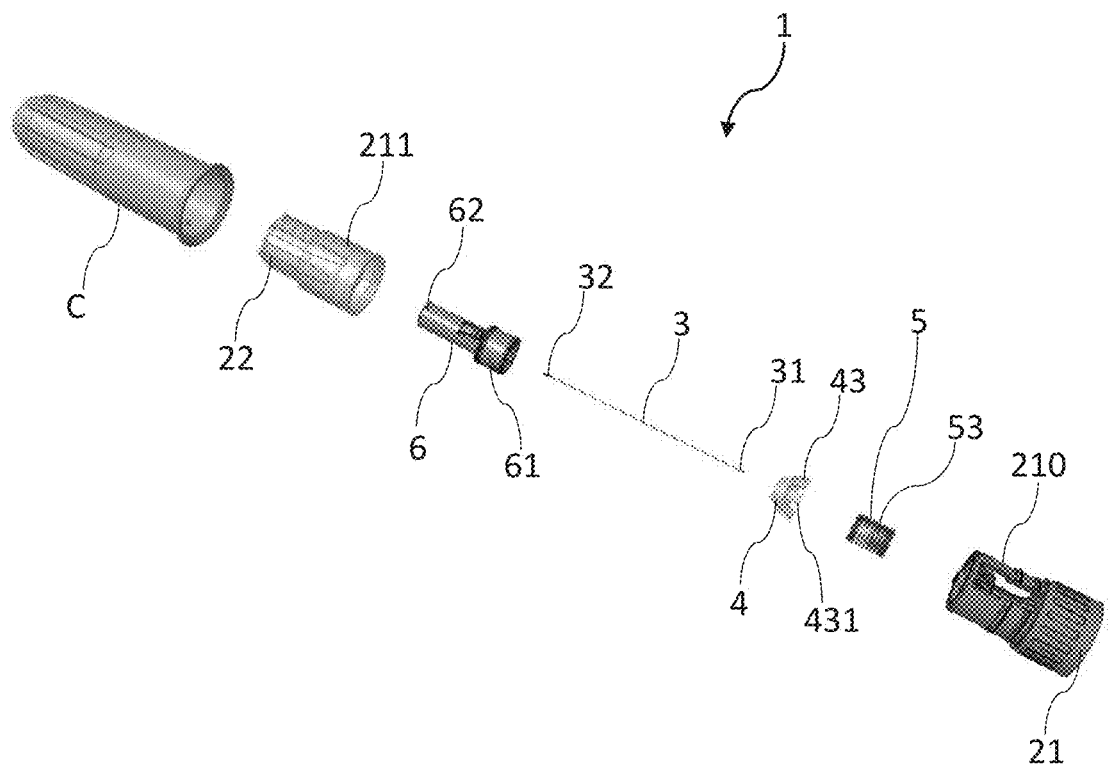
FIG. 1 is an exploded view of the safety pen needle according to this invention.
Figure 2:
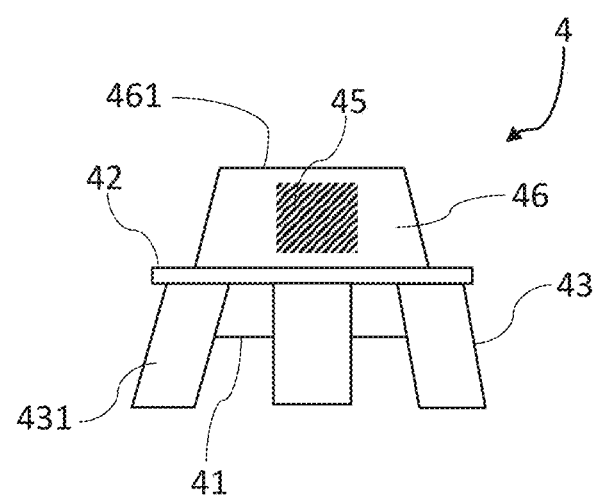
FIG. 2 is a schematic side view of a component of the safety pen needle of FIG. 1.
Figure 3:
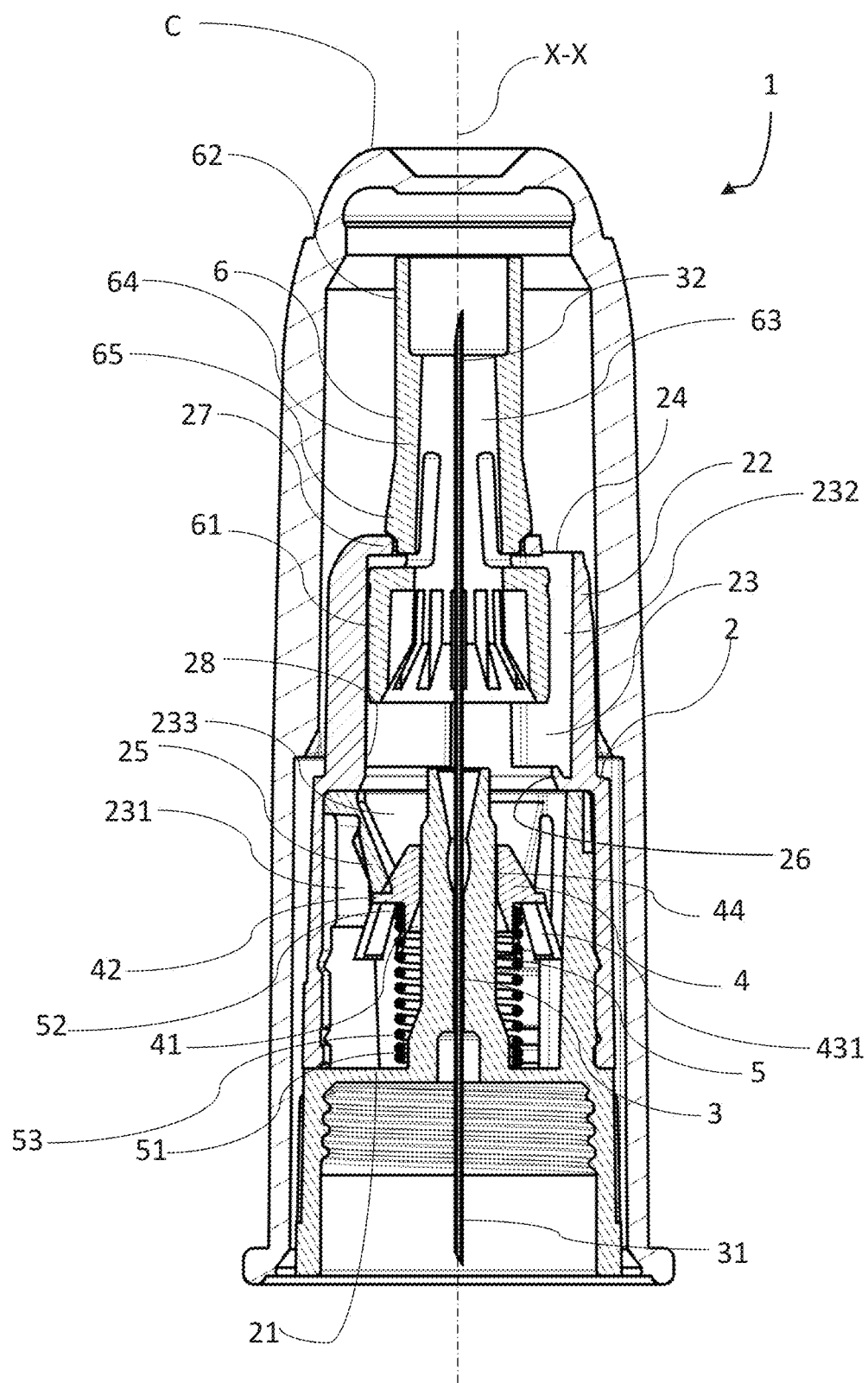
FIG. 3 is a sectional view of the pen needle of FIG. 1 in a first configuration.
Figure 4:
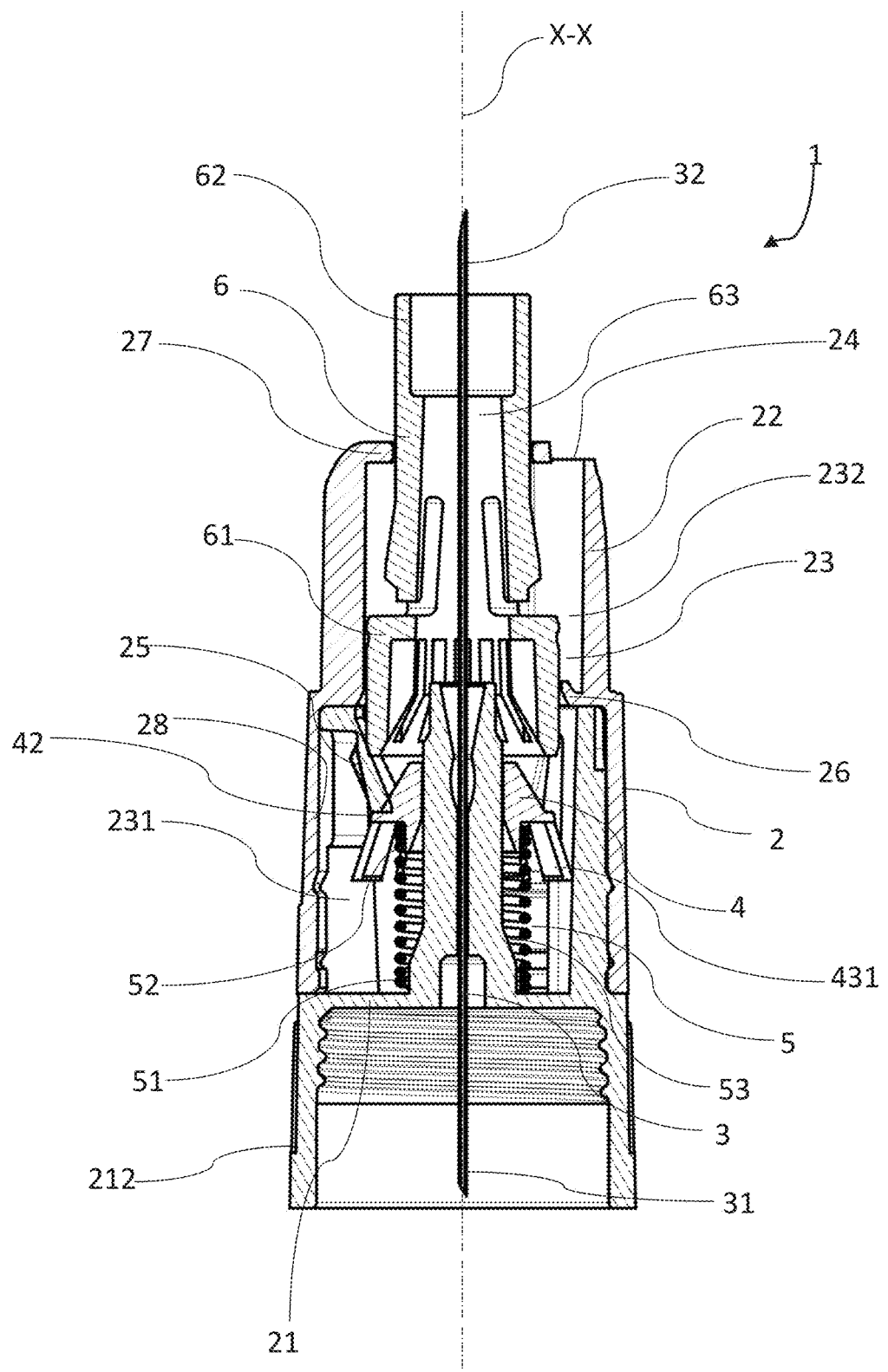
FIG. 4 is a sectional view of the pen needle of FIG. 1 in an intermediate configuration.
Figure 5:
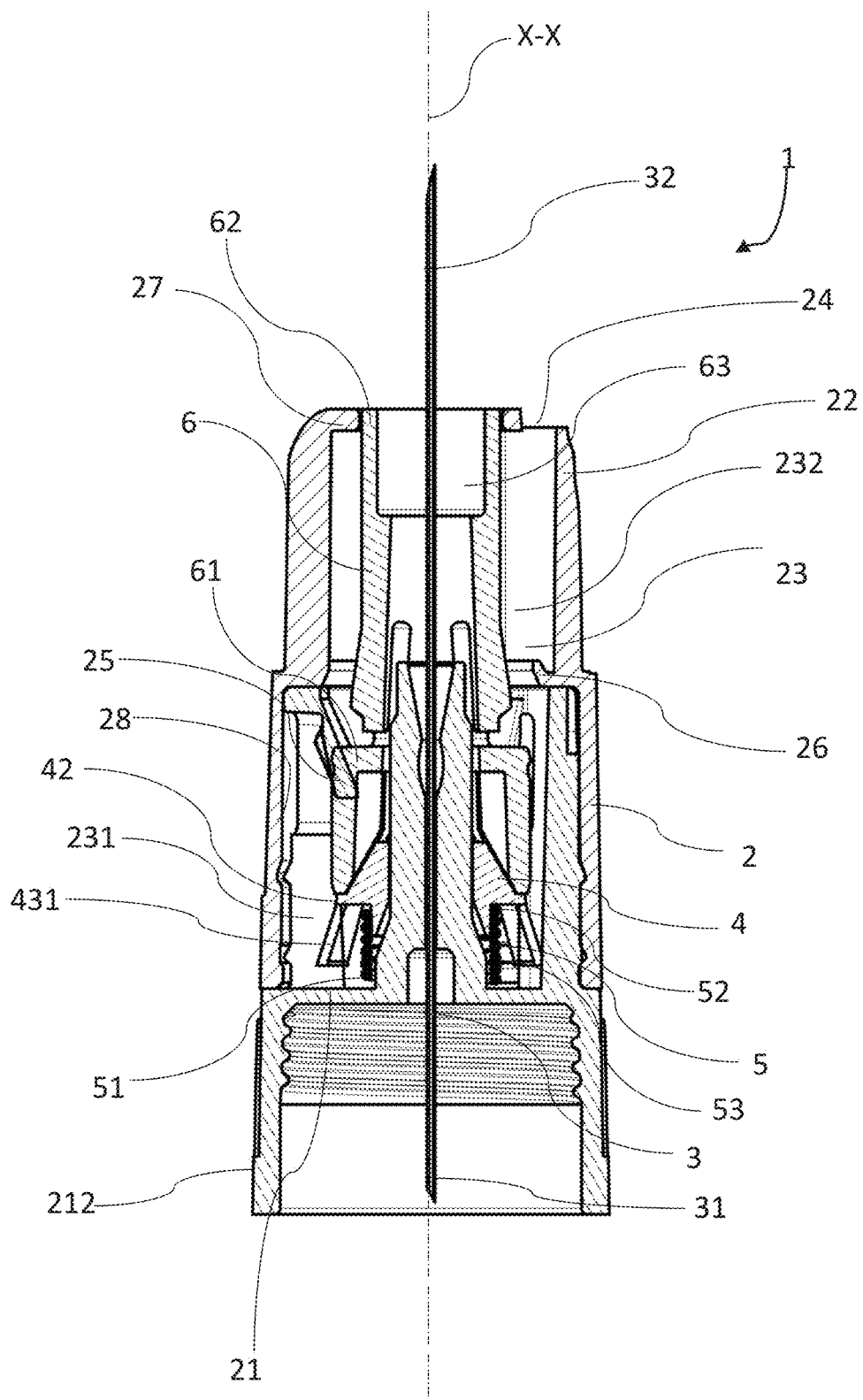
FIG. 5 is a sectional view of the pen needle of FIG. 1 in a second configuration.
Figure 6:
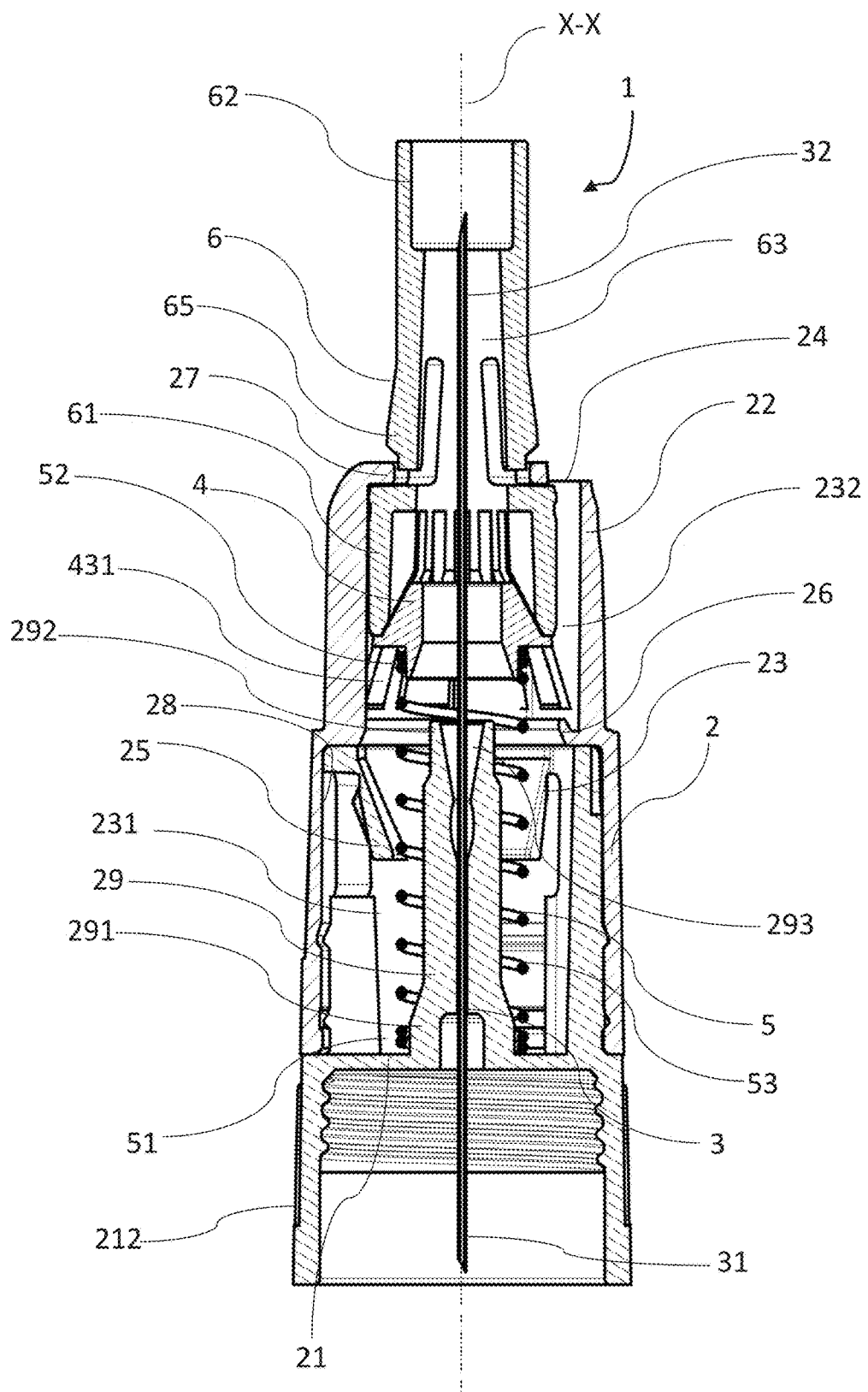
FIG. 6 is a sectional view of the pen needle of FIG. 1 in a third configuration.

With reference to the annexed figures, numeral 1 designates a safety pen needle. In its preferred embodiment, the safety pen needle 1 comprises a main body 2 which extends in a longitudinal direction X-X between a bottom 21 and an opposite top 22. Preferably, the main body 2 has a substantially cylindrical shape. In detail, the main body 2 comprises a cavity 23 which extends from the bottom 21 to an opening 24 placed at the top 22. In other words, the cavity 23 of main body 2 is a blind cavity. Preferably, the cavity 23 has a cylindrical shape coaxial with the main body 2.

The main body 2 also comprises first elastic elements 25 placed inside the cavity 23 at a lower portion 231 of the cavity 23 proximate to the bottom 21 and an interference element 26 placed at an upper portion 232 of the cavity 23 proximate to the top 22. In more detail, lower portion 231 extends from the bottom 21 of the main body 2 to an intermediate portion 233 of the cavity 23 placed between the bottom 21 and the top 22 of the main body 2. In contrast, the upper portion 232 of the cavity 23 extends from the intermediate portion 233 to the top 22 of the main body 2. In the embodiment of FIG. 1, main body 2 comprises a single first elastic element 25 and a single interference element 26. According to a preferred embodiment, the main body 2 comprises a plurality of first elastic elements 25 placed along the profile of the cavity 23 at the lower portion 231 of the cavity 23 and a plurality of interference elements 26 placed along the profile of the cavity 23 at the upper portion 232 of the cavity 23.

The safety pen needle 1 also comprises a cannula 3 fixed to the main body 2 and extending in the longitudinal direction X-X between a lower end 31 placed proximate to the bottom 21 of the main body 2 and an opposite top end 32, at least partially projecting out of the cavity 23 through the opening 24. Preferably, the cannula 3 is fixed to the main body 2 through a sleeve 29. Said sleeve 29 is placed inside the cavity 23 and is connected to the bottom 21 of the main body 2. More preferably, the sleeve 29 extends between a bottom 291 of the sleeve 29, connected to the bottom 21 of the main body 2, and an opposite top 292 of the sleeve 29 in a longitudinal direction X-X. In addition, the sleeve 29 comprises a pass-through cavity 293 from the bottom 291 to the top 292 of the sleeve 29, configured to stably house the cannula 3. The cannula 3 is then inserted into the pass-through cavity 293 of the sleeve 29 to be stably placed inside the cavity 23 of the main body 2 maintaining the upper end 31 over the opening 24. In other words, the cannula 3 is stably secured to the interior of the pass-through cavity 293 of the sleeve 29.

According to the preferred embodiment of the invention shown in the annexed figures, the main body 2 comprises a skirt 212 projecting out of the bottom 21 in order to define a recess within which the lower end 31 of the cannula 3 is housed. In fact, the lower end 31 of the cannula 3 goes through the bottom and comes out of it remaining confined inside the recess defined by the skirt 212. This way, the lower end 31 of the cannula 3 cannot be easily reached by the user's fingers reducing the risk of accidental punctures. Preferably, the skirt 212 preferably comprises a threaded portion 213 on its inner wall, namely on the wall that defines the recess. The threaded portion 213 of the skirt 212 is configured to be screwed to the corresponding threaded portion 101 created on the outer collar of a vial 10 containing a liquid to be injected.

In addition, the safety pen needle 1 comprises a lock element 4 placed inside the cavity 23 of the main body 2 comprising a lower counteracting portion 41 and an upper abutment portion 42. Preferably, the lock element 4 comprises an abutment body 46 which extends from the upper abutment portion 42 to an opposite top 461 of the abutment body 46 in the longitudinal direction X-X. In the preferred embodiment, the upper abutment portion 42 is shaped as a flange projecting out of the abutment body 46 along a transverse direction with respect to the longitudinal direction X-X. Still preferably, the lower counteracting portion 41 projects out of the abutment body 46 from the upper abutment portion 42 in the longitudinal direction X-X towards the bottom 21 of the main body 2.

The lock element 4 also comprises engagement means 43 placed at the lower counteracting portion 41. In the preferred embodiment, the engagement means 43 are deformable and project out of the upper abutment portion 42 towards the bottom 21 of the main body 2.

The lock element 4 comprises a first through channel 44 extending from the lower counteracting portion 41 to the upper abutment portion 42. More in detail, the first through channel 44 extends in the longitudinal direction X-X from the lower counteracting portion 41 to the top 461 of the abutment body 46. The cannula 3 is inserted into the first through channel 44. Preferably, the first channel 44 has a bigger diameter than the diameter of the sleeve 29. This way the cannula 3 is coaxially inserted into the sleeve 29, which is in turn coaxially inserted into the first channel 44 allowing the lock element 4 to slide along the sleeve 29.

In addition, the safety pen needle 1 comprises a thrust element 5 placed inside the cavity 23 of the main body 2 and extending in the longitudinal direction X-X between a first end 51 and an opposite second end 52. In detail, the first end 51 is fixed proximate to the bottom 21 of the main body 2, while the second end 52 is connected to the lower counteracting portion 41 to push the lock element 4 toward the top 22 of the main body 2. In other words, the thrust element 5 is configured to push the lock element 4 along the longitudinal direction X-X from the bottom 21 towards the top 22 of the main body 2.

The safety pen needle 1 also comprises a shield 6 which extends in the longitudinal direction X-X between a lower lock portion 61 and an opposite upper cover portion 62. More in detail, the shield 6 comprises a shield body 64 which extends in the longitudinal direction X-X from the lower lock portion 61 to the upper cover portion 62. The shield 6 comprises a second through channel 63 extending from the lower lock portion 61 to the upper cover portion 62.

In detail, the cannula 3 is inserted into the second through channel 63. The shield 6 is movable relative to the main body 2 in the longitudinal direction X-X while remaining at least partially inserted within the cavity 23 of the main body 2. In other words, the shield 6 is movable in the longitudinal direction X-X between a first position where the lower lock portion 61 is inserted into the cavity 23 while the upper cover portion 62 is placed outside the cavity 23 beyond the opening 24 in order to cover the top end 32 of the cannula 3, and a second position where the shield body 64 is completely inserted into the cavity 23 in order to expose the top end 32 of the cannula 3 beyond the opening 24. In addition, the shield 6 is movable in the longitudinal direction X-X from the second position to a third position where the upper cover portion 62 is placed outside the cavity 23 beyond the opening 24 to cover the opposite top end 32 of the cannula 3.

As it will become clear in this description, the first and the third position have a different distance along the longitudinal axis X-X of the upper cover portion 62 from the opening 24. In particular, said distance along the longitudinal axis X-X of the upper cover portion 62 from the opening 24 is bigger in the third position compared to the first position.

The safety pen needle 1 is configured to move from a first configuration to a second configuration. In detail, in the first configuration the first elastic elements 25 engage the upper abutment portion 42 to maintain the lock element 4 in the lower portion 231 of the cavity 23. In other words, the contact between the first elastic elements 25 and the upper abutment portion 42 of the lock element 4 in the first configuration contrasts the thrust action towards the top 22 of the thrust element 5. In fact, as previously mentioned, the thrust element 5 is configured to apply a thrust action on the lock element 4 toward the top 22 of the main body 2. In the first configuration, the lock element 4 is therefore maintained in the lower portion 231 of the cavity 23. Still in the first configuration, the shield 6 is in the first position, namely it projects out of the cavity 23 through the opening 24 to entirely cover the upper end 32 of the cannula 3. On the contrary, in the second configuration, the shield 6 is in the second position. Advantageously, in the first configuration, the upper cover portion 62 of the shield 6 protects the top end 32 of the cannula 3, therefore avoiding accidental punctures.

The safety pen needle is configured to move from the first configuration to the second configuration when the shield 6 moves towards the bottom 21 of the main body 2 under the action of an external thrust. In other words, the movement from the first to the second configuration happens during use, namely when an external user places the safety pen needle 1 on the skin of a patient to perform an injection. When pushing the pen needle 1 on the patient's skin, the external thrust needed to allow the safety pen needle 1 to move from the first to the second configuration is generated. In fact, when the pen needle 1 is pushed towards the skin, the upper cover portion 62 of the shield 6 comes into contact with the skin pushing said shield 6 towards the bottom 21 of the main body 2 until the shield 6 reaches its second position, therefore moving the pen needle 1 in the second configuration. It shall be noted that, while the shield 6 falls towards the bottom 21 of the main body retracting inside it, the top end 32 of the cannula 3 is gradually exposed penetrating inside the skin under the external thrust imparted to the pen needle. For example, the external thrust is imparted on the pen needle, when in use, by a user who performs an injection having previously mounted the pen needle 1 on a vial 10 which is in turn mounted on an injection pen.

In particular, in the second configuration the lower lock portion 61 is irreversibly coupled to the lock element 4 placed at the lower portion 231 of the cavity 23 to expose the upper end 32 of the cannula 3 through the opening 24. In detail, in the second configuration the abutment body 46 of the lock element 4 is locked inside the second through channel 63 at the lower lock portion 61 of the shield 6. In further detail, in the second lower counteracting configuration, the shield 6 is in the second position.

The movement of the shield 6 from the first to the second position determines the compression of the thrust element 5 towards the bottom 21 of the main body 2.

In addition, the pen needle 1 is configured to move from the second configuration to a third configuration due to the thrust exerted by the thrust element 5 on the lock element 4. In the third configuration, the engagement means 43 are abutting on the interference element 26 to maintain the lock element 4 irreversibly locked in the upper portion 232 of the cavity 23 while the shield 6 is in the third position where it projects out of the cavity 23 through the opening 24 to entirely cover the upper end 32 of the cannula 3. Therefore, the third configuration of the pen needle is irreversible. Advantageously, in the third configuration the shield 6 covers the upper end 32 of the cannula 3 irreversibly preventing accidental punctures and reuse of the same pen needle 1 by a user.

When in use, after the injection, the safety pen needle 1 is removed from the patient's skin. Following removal of the safety pen needle 1, the thrust element 5, thrusting the lock element 4 towards the top 22, moves also the shield 6 to the third position, allowing the safety pen needle 1 to automatically move from the second configuration to the third configuration.

In other words, following the removal of the safety pen needle 1 from the skin, the shield 6 moves from the second to the third position.

As mentioned before, in the third configuration, the shield 6 is irreversibly locked in the third position. In fact, the engagement means 43 lock in contact with the interference element 26 and prevent the shield 6 from subsequently moving from the third to the second position. This way, the upper cover portion 62 of the shield 6 permanently protects the top end 32 of the cannula 3 avoiding reuse of the same pen needle and eventual accidental punctures.

According to a preferred embodiment, the main body 2 comprises a lip 27 located at the opening 24. Said lip 27 is configured to engage the lower lock portion 61 of the shield 6 in the third configuration to stably hold the shield 6 at least partially inserted inside the cavity 23. Preferably, the lip 27 projects out of the main body 2 above the cavity 23 along a transverse direction with respect to the longitudinal direction X-X. In particular, the contact between the lip 27 and the lower lock portion 61 of the shield 6 prevents the shield 6 to come out beyond the opening 24. In other words, the contact between the lip 27 and the lower lock portion 61 maintains the shield 6 in the third position.

According to an alternative and/or combinable embodiment to/with the previous one, the shield 6 comprises at least one second elastic element 65 interposed between the lower lock portion 61 and the upper cover portion 62. The lip 27 is configured to engage the second elastic element 65 in the first configuration so as to stably hold the shield 6 at least partially inserted inside the cavity 23. The contact between the lip 27 and the second elastic element 65 prevents the shield 6 from entering inside the cavity 23 without an external thrust. In other words, the contact between the lip 27 and the second elastic element 65 maintains the shield 6 in the first position when there is no external thrust. Conversely, an external thrust imparted on the shield 6 directed towards the bottom 21 determines the deformation of the second elastic element 65 in contact with the lip 27 in order to allow the shield 6 to move from the first to the second position.

As observable in the attached figures, in the first position the lower lock portion 61 is spaced from the lip 27, while the second elastic element 65 is in contact with the lip 27. Conversely, in the third position the lower lock portion 61 is in contact with the lip 27, while the second elastic element is spaced from the lip 27. It follows that, in the third position, the distance in the longitudinal direction X-X of the upper cover portion 62 of the shield 6 from the opening 24 is greater than in the first position.

It shall also be noted that it is possible to modify the stiffness of the second elastic element 65 to modify the intensity of the thrust action required to allow the pen needle 1 to switch from the first to the second configuration. For example, the greater the stiffness of the second elastic element 65, the greater the strength needed to disengage the second elastic element 65 from the lip 27. In addition, by changing the geometrical shape of the second elastic element 65 and the lip 27 it is equally possible to modify the intensity of the external thrust necessary to disengage the second elastic element 65 from the lip 27. In the preferred embodiment, the cavity 23 is delimited by an inner surface 28 of the main body 2. The first elastic elements 25 project out of the inner surface 28 at the lower portion 231 of the cavity 23, while the interference element 26 projects out of the inner surface 28 at the upper portion 232 of the cavity 23. Preferably, the first elastic elements 25 project out of the inner surface 28 toward the bottom 21 of the main body 2.

The interference element 26 instead projects out of the inner surface 28 toward the top 22 of the main body 2.

In the preferred embodiment, the thrust element 5 comprises a helical spring 53. The helical spring 53 is placed between the first end 51 and the second end 52 of the thrust element 5.

Preferably, the helical spring 53 is configured to take, in the longitudinal direction X-X, a first length, a second length and a third length respectively in the first, second and third configuration. In detail, the first length is greater than the second length, while the third length is greater than the first and second lengths. In other words, the movement from the first to the second configuration determines a compression of the helical spring 53, while the movement from the second to the third configuration happens through the extension of the helical spring 53.

In further detail, when moving from the first to the second configuration, the lower lock portion 61 of the shield 6 contacts the first elastic elements 25 and bends them toward the inner surface 28 of the main body 2 to thereby disengage the lock element 4 from the first elastic elements 25 and push the lock element 4 toward the bottom 21 to compress the helical spring 53 toward the bottom 21 of the main body 2. In other words, during the movement between the first and the second configuration the shield 6 determines a deformation of the first elastic elements 25 toward the inner surface 28. Said deformation of the first elastic elements 25 allows for the disengagement of the lock element 4 from the first elastic elements 25. Said first elastic elements 25 can be manufactured with materials of different stiffness or with the same material with different sections. The thrust of the lock element 4 toward the bottom 21 of the main body 2 determines the compression of the helical spring 53, which therefore takes the second length.

In the preferred embodiment, the lock element 4 and the second through channel 63 at the lower lock portion 61 have a frustoconical shape and are complementary to each other such that, in the second and third configurations, the lock element 4 will be stuck inside the second channel 63 at the lower lock portion 61 by frustoconical fit with interference. In other words, as previously mentioned, when moving from the first to the second configuration, the lock element 4 is thrusted toward the bottom 21 of the main body 2. Once the thrust element 5 reaches the end of stroke, the shield 6 is thrusted toward the bottom 21, the lock element 4 progressively inserts into the second through channel 63 until the lock element 4 will be irreversibly stuck inside the second through channel 63 at the lower lock portion 61.

In the preferred embodiment, the engagement means 43 of the lock element 4 comprise a plurality of deformable fins 431. Preferably, the deformable fins 431, when moving from the third to the second configuration, switch between a rest configuration and a deformed configuration as a result of the deformation imposed by the interference element 26. In the movement from the rest configuration to the deformed configuration the deformable fins 431 are compacted together. In other words, during the movement from the second to the third configuration, the interference element 26 compresses the deformable fins 431 toward the lower counteracting portion 41 allowing the movement of the lock element 4 from the lower portion 231 to the upper portion 232 of the cavity 23. As they pass the interference element 26, the deformable fins 431 are switched from the deformed configuration to the rest configuration due to the springback effect. In other words, due to the springback effect, the deformable fins 431 expand away from the lower counteracting portion 41. The contact between the interference element 26 and the deformable fins 431 locks the lock element 4 in the upper portion 232 of the cavity 23. In addition, as already mentioned, the shield 6 cannot come out of the main body, preferably because of the lip 27 engaging the lower lock portion 61 of the shield 6 in order to stably maintain the shield 6 at least partially inserted into the cavity 23. Therefore, in the third configuration of the pen needle 1, both the lock element 4 and the shield 6 stay locked in the upper portion 232 of the cavity 23. Advantageously, in the third configuration the top end 32 of the cannula 3 is irreversibly covered by the shield 6 avoiding accidental punctures and reuse of the same pen needle 1.

In an alternative embodiment, the main body 2 comprises a lower body 210 and an upper body 211 which are coaxial with each other and stably coupled together to define the cavity 23 therein. In particular, the lower body 210 defines the lower portion 231 of the cavity 23, while the upper body 211 defines the upper portion 232 of the cavity 23. Preferably, the lower body 210 and the upper body 211 are stably coupled by threaded fit. More in detail, the lower body 210 has a male threading configured to be coupled with the female threading of the upper body 211. However, alternative embodiments are contemplated where the lower body 210 has a female threading configured to be coupled with the male threading of the upper body 211.

More preferably, the lower body 210 is opaque, the upper body 211 is at least partly transparent and the lock element 4 comprises at least one colored portion 45.

In particular, in the first and second configurations, the lower body 210 screens the colored portion 45 of the lock element 4 located in the lower portion 231 of the cavity 23. As previously mentioned in the first and second configuration, the lock element 4 stays in the lower portion 231 of the cavity 23. Since the lower portion 231 of the cavity 23 is defined on the lower body 210, said lower body 210 screens the lock element 4.

In addition, in the third configuration, the colored portion 45 of the lock element 41 locked in the upper portion 232 of the cavity 23 is visible from the outside through the upper body 211. As previously mentioned, in the third configuration the lock element 4 stays locked in the upper portion 232 of the cavity 23. Since the upper portion 232 of the cavity 23 is defined on the upper body 211, the colored portion 45 of the lock element 4 is visible through the transparent portion of the upper body 211.

Advantageously, the possibility of being able to see from the outside the lock element 4 only in the third configuration allows the user to identify a visual signal confirming the correct activation of the mechanism mentioned above, namely the safety mechanism which prevents the pen needle to move from the third to the second configuration. For example, the possibility to see from the outside the lock element 4 only in the third configuration allows the user to understand if the safety pen needle 1 has already been used. In the same manner, if the colored portion 45 of the lock element 4 is screened, this means that the pen needle 1 has not been used yet. Conversely, if the colored portion 45 of the pen needle 1 is visible through the upper body 211 it means that the pen needle 1 has already been used.

According to a preferred embodiment of this invention, the pen needle 1 comprises a cap C which can be coupled with the main body 2 to protect the shield 6 in the first configuration and, optionally, in the third configuration. While in use, the cap C is removed to expose the shield 6 in order to allow the user to perform the injection and the sequential movement of the pen needle between the first, the second and the third configuration.

Figure 7:
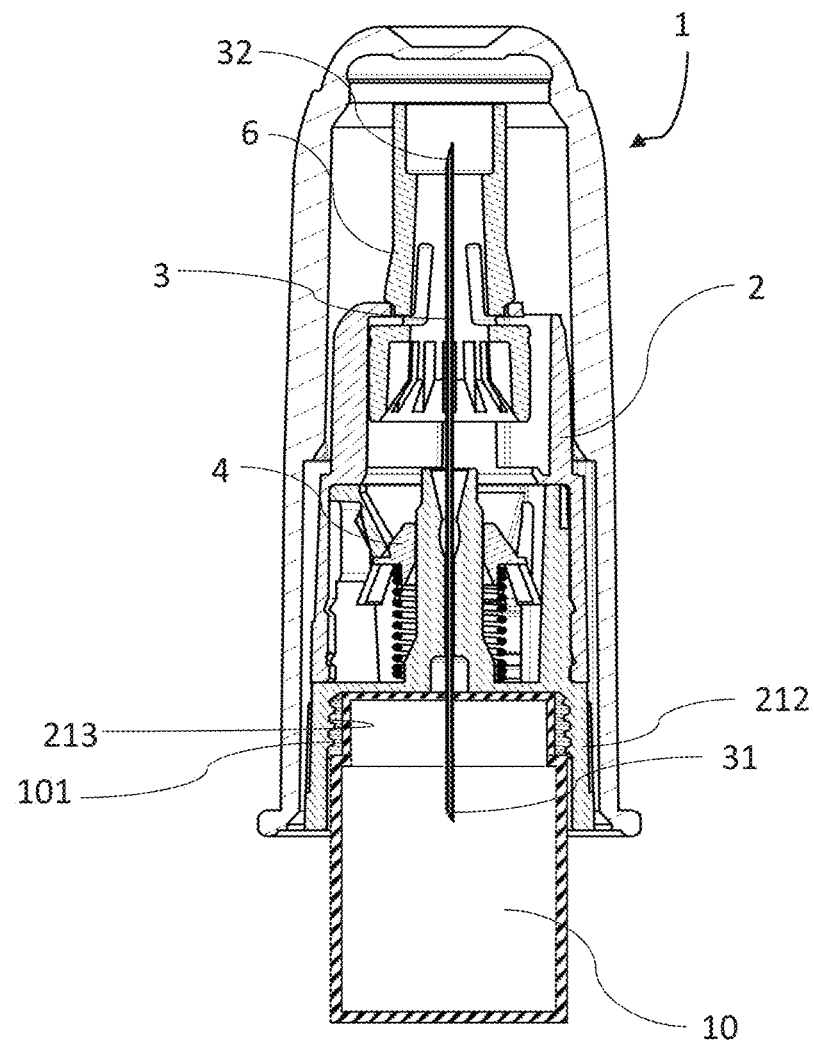
FIG. 7 is a sectional view of an injection kit in an assembled configuration.

This invention also intends to describe an injection kit, represented in FIG. 7. In detail, said kit comprises a safety pen needle 1 as previously described in accordance with any of its embodiments.

In addition, said kit comprises a vial 10 containing a liquid to be injected. The vial 10 is adapted to be coupled to the bottom 21 of the main body 2, to thereby allow the cannula 3 to withdraw the liquid to be injected. Preferably, said vial 10 is coupled to the skirt 212 via a threaded connection. In other words, in case of use, the vial 10 is coupled to the skirt 212 at the bottom 21 of the main body 2 of the pen needle 1. As already mentioned, the threaded portion 213 of the skirt 212 is configured to be screwed on the corresponding threaded portion 101 created on the outer collar of the vial 10. This way, the lower end 31 of the cannula 3 is inserted into the vial 10 in order to withdraw the liquid contained inside the vial 10. It shall be noted how the vial 10 can be coupled to an injection pen in order to allow said pen to exert a pressure on the fluid contained in the vial 10 to perform the injection when the pen needle 1 is in the second configuration where the upper end 32 of the cannula 3 is inserted under the skin. In fact, in the second configuration the shield 6 is retracted inside the cavity 23 of the main body 2 as an effect of the thrust caused by contact with the skin, while the upper end 32 of the cannula 3 is exposed and subcutaneously inserted.

The invention claimed is:

1. A safety pen needle, comprising:
   a main body which extends in a longitudinal direction between a bottom and an opposite top, the main body comprising a cavity which extends from the bottom to an opening at the top, the main body further comprising first elastic elements inside the cavity at a lower portion of the cavity proximate to the bottom and an interference element at an upper portion of the cavity proximate to the top;
   a cannula fixed to the main body and extending in the longitudinal direction between a lower end proximate to the bottom of the main body and an opposite top end at least partially projecting out of the cavity through the opening;
   a lock element, inside the cavity of the main body, comprising a lower counteracting portion, an upper abutment portion, and engagement means at the lower counteracting portion, the lock element further comprising a first through channel extending from the lower counteracting portion to the upper abutment portion, wherein the cannula is inserted into the first through channel;
   a thrust element inside the cavity of the main body which extends in the longitudinal direction between a first end and an opposite second end, wherein the first end is fixed proximate to the bottom of the main body, and wherein the second end is connected to the lower counteracting portion to push the lock element toward the top of the main body; and
   a shield which extends in the longitudinal direction between a lower lock portion and an opposite upper cover portion, the shield comprising a second through channel extending from the lower lock portion to the upper cover portion, wherein the cannula is inserted into the second through channel, wherein the shield is movable relative to the main body in the longitudinal direction while remaining at least partially inserted within the cavity of the main body;
   wherein the safety pen needle is configured to move from a first configuration, in which the first elastic elements engage the upper abutment portion to maintain the lock element in the lower portion of the cavity while the shield projects out of the cavity through the opening to entirely cover the top end of the cannula, to a second configuration when the shield moves toward the bottom of the main body under action of external thrust,
   wherein in the lower lock portion, in the second configuration, is irreversibly coupled to the lock element at the lower portion of the cavity to expose the top end of the cannula through the opening,
   wherein the safety pen needle is further configured to move from the second configuration to a third configuration due to action of thrust exerted by the thrust element,
   wherein the engagement means, in the third configuration, abuts the interference element to maintain the lock element irreversibly locked in the upper portion of the cavity while the shield projects out of the cavity through the opening to entirely cover the top end of the cannula,
   wherein the main body further comprises a lip located at the opening,
   wherein the lip is configured to engage the lower lock portion of the shield in the third configuration to stably hold the shield at least partially inside the cavity,
   wherein the shield further comprises at least one second elastic element interposed between the lower lock portion and the upper cover portion, and
   wherein the at least one second elastic element is configured to engage the lip in the first configuration so as to stably hold the shield at least partially inside the cavity.

2. The safety pen needle of claim 1, wherein the cavity is delimited by an inner surface of the main body,
   wherein the first elastic elements projects out of the inner surface at the lower portion of the cavity, and
   wherein the interference element projects out of the inner surface at the upper portion of the cavity.

3. The safety pen needle of claim 1, wherein the thrust element comprises a helical spring.

4. The safety pen needle of claim 3, wherein the helical spring is configured to take, in the longitudinal direction, a first length, a second length, and a third length, in the first, second, and third configurations respectively,
   wherein the first length is greater than the second length, and
   wherein the third length is greater than the first length or the second length.

5. The safety pen needle of claim 3, wherein when moving from the first configuration to the second configuration, the lower lock portion of the shield contacts the first elastic elements and bends the first elastic elements toward an inner surface of the main body to thereby disengage the lock element from the first elastic elements and to push the lock element toward the bottom of the main body to compress the helical spring toward the bottom of the main body.

6. The safety pen needle of claim 1, wherein the lock element and the second through channel at the lower lock portion have a frustoconical shape and are complementary to each other such that, in the second and third configurations, the lock element will be stuck inside the second through channel at the lower lock portion by frustoconical fit.

7. The safety pen needle of claim 1, wherein the engagement means of the lock element comprises a plurality of deformable fins.

8. The safety pen needle of claim 7, wherein when moving from the second configuration to the third configuration, the deformable fins are switched between a rest configuration and a deformed configuration as a result of deformation imposed by the interference element,
  wherein as they move from the rest configuration to the deformed configuration, the deformable fins are compacted together, and
  wherein as they pass the interference element, the deformable fins are switched from the deformed configuration to the rest configuration due to a springback effect.

9. The safety pen needle of claim 1, wherein the main body further comprises a lower body and an upper body, which are coaxial with each other and stably coupled together to define the cavity therein,
  wherein the lower body defines the lower portion of the cavity, and
  wherein the upper body defines the upper portion of the cavity.

10. The safety pen needle of claim 9, wherein the lower body is opaque,
  wherein the upper body is at least partially transparent, and
  wherein the lock element comprises at least one colored portion.

11. The safety pen needle of claim 10, wherein in the first and second configurations, the lower body screens the at least one colored portion of the lock element located in the lower portion of the cavity.

12. The safety pen needle of claim 10, wherein in the third configuration, the at least one colored portion of the lock element locked in the upper portion of the cavity is visible from outside the safety pen needle through the upper body.

13. An injection kit, comprising:
  the safety pen needle of claim 1; and
  a vial containing a liquid to be injected, wherein the vial is configured to be coupled to the bottom of the main body, to thereby allow the cannula to withdraw the liquid to be injected.

* * * * *